(12) United States Patent
Demuth et al.

(10) Patent No.: US 6,559,314 B2
(45) Date of Patent: May 6, 2003

(54) METHOD FOR THE PRODUCTION OF THIAZOLIDIN

(75) Inventors: Hans-Ulrich Demuth, Halle/Saale (DE); Susanne Kruber, Halle/Saale (DE)

(73) Assignee: Probiodrug AG (DE)

( * ) Notice: Subject to any disclaimer, the term of this patent is extended or adjusted under 35 U.S.C. 154(b) by 0 days.

(21) Appl. No.: 10/012,786

(22) Filed: Dec. 10, 2001

(65) Prior Publication Data
US 2002/0082427 A1 Jun. 27, 2002

Related U.S. Application Data

(63) Continuation of application No. PCT/EP00/03213, filed on Apr. 11, 2000.

(30) Foreign Application Priority Data

Jun. 10, 1999 (DE) ......................................... 199 26 233

(51) Int. Cl.$^7$ ............................................. C07D 227/04
(52) U.S. Cl. ....................................................... 548/146
(58) Field of Search ........................................... 548/146

(56) References Cited

U.S. PATENT DOCUMENTS

| | | | |
|---|---|---|---|
| 2,961,377 A | 11/1960 | Shapiro et al. | ................ 167/65 |
| 3,960,949 A | 6/1976 | Ahrens et al. | .......... 260/564 B |
| 4,935,493 A | 6/1990 | Bachovchin et al. | ....... 530/331 |
| 5,433,955 A | 7/1995 | Bredehorst et al. | ......... 424/94.3 |
| 5,512,549 A | 4/1996 | Chen et al. | .................... 514/12 |
| 5,614,379 A | 3/1997 | MacKellar | ................. 435/68.1 |
| 5,624,894 A | 4/1997 | Bodor | ............................ 514/2 |
| 6,006,753 A | 12/1999 | Efendic | ...................... 128/898 |

FOREIGN PATENT DOCUMENTS

| | | | | |
|---|---|---|---|---|
| DE | DT 25 42598 A1 | 4/1976 | ......... | C07C/129/16 |
| DE | 196 16 486 A1 | 10/1997 | ......... | A61K/39/395 |
| FR | 2085665 | 3/1971 | ......... | A61K/27/00 |
| FR | 2696740 | 10/1992 | ....... | C07D/207/404 |
| JP | 4334357 | 11/1992 | ......... | C07C/233/57 |
| WO | WO 93/08259 | 4/1993 | | |
| WO | WO 95/11689 | 5/1995 | .......... | A61K/37/00 |
| WO | WO 95/15309 | 6/1995 | ......... | C07D/207/16 |
| WO | WO 95/29691 | 11/1995 | .......... | A61K/38/00 |
| WO | WO 97/40832 | 11/1997 | ......... | A61K/31/425 |
| WO | WO 97/45117 | 12/1997 | ......... | A61K/31/435 |
| WO | WO 98/22494 | 5/1998 | ............ | C07K/5/06 |
| WO | WO00/01849 | 1/2000 | ............ | C12Q/1/68 |
| WO | WO 00/53171 | 9/2000 | .......... | A61K/31/155 |
| WO | WO01/62266 A2 | 8/2001 | .......... | A61K/38/00 |

OTHER PUBLICATIONS

Campbell, I.W. New Antidiabetic Drugs, ed. C.J. Bailey & P.R. Flatt, Smith–Gordon, "Sulphonylureas and metformin: efficacy and inadequacy". 3:33–51 (1990).
Mercla Index, 11$^{th}$ Edition, p. 934.

Martindale The Extra Pharmacopeia, 30$^{th}$ Edition, Pharmaceutial Press, 1993, p. 1619.

Chemical Abstracts, vol. 115. No. 15, Oct. 14, 1991 Columbus, Ohio, US; abstract No. 149947q, Schoen Ekkehard Et Al: "Dipeptidyl peptidase IV in the immune system. Effects of specific enzyme inhibitors on activity of dipeptidyl peptidase IV and proliferation of human lymphocytes".

Chemical Abstracts, vol. 126, No. 2, Jan. 13, 1997 Columbus, Ohio, US; abstract No. 16161j, Stoeckel A. Et Al: "Competitive inhibition of proline specific enzymes by amino acid thioxopyrrolidides and thiazolidides".

Chemical Abstracts, vol. 118, No. 25, Jun. 21, 1993 Columbus, Ohio, US; abstract No. 255342k, Hosoda, et al, "Preparation of N–(heterocyclic Carbonyl) Amino Acids and Analogs as Prolyl Endopeptidase Inhibitors", Nov. 1992 (Nov. 20, 1992).

Arai Et Al: "Synthesis of prolyl endopeptidase inhibitors and evaluation of their structure–activity relationships : in vitro inhibition of prolyl endopeptidase from Canine Brain" Chemical and Pharmaceutical Bulletin., Bd. 41, No. 9, 1993, pp. 1583–1588.

J. Lin et al.: "Inhibition of depeptidyl peptidase IV by fluoroolefin–containing n–peptidyl–O–hydroxylamine peptidomimetics" Proceedings of the National Academy of Sciences of USA, vol. 95, Nov. 1998, pp. 14020–14024.

(List continued on next page.)

*Primary Examiner*—Bruck Kifle
(74) *Attorney, Agent, or Firm*—Thomas M. Saunders; Brown Rudnick Berlack Israels, LLP

(57) ABSTRACT

The invention relates to a simple and industrially readily executable method of producing thiazolidine base and salts thereof. In particular, the invention relates to a process for the production of thiazolidine base and salts thereof which is characterized in that hexamethylenetetramine of formula (I)

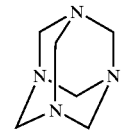

Figure 1:
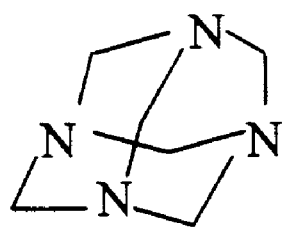

is caused to react with cysteamine or salts thereof of formula (II)

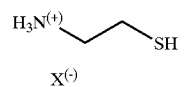

in which X$^{(-)}$ represents an acid residue, X$^{(-)}$ being preferably a halide or sulfate.

12 Claims, 2 Drawing Sheets

OTHER PUBLICATIONS

Korom, S., et al "Inhibition of CD26/dipeptidyl peptidase IV activity in vivo prolongs cardiac allograft survival in rat recipients", Transplantation vol. 63, 1495–1500 No. 10 (1997).

Tanka, S., et al., "Supperession of arthritis by the inhibitors of dipeptidyl peptidase IV". Int. J. Immunopharmacol, vol. 19, No. 1 pp. 15–24, 1997.

Mentlein, R., et al., "Proteolytic processing of neuropeptide Y and peptide YY by dipeptidyl peptidase IV". Regul. Pept. 49, 133–144(1993).

Wetzl, W., et al., "Effects of the CLIP fragment ACTH 20–24 on the duration of REM sleep episodes". Neuropeptides, 31, 41–45 (1997).

Amasheh, S., et al., "Electrophysiological analysis of the function of the mammalian renal peptide transporter expressed in Xenopus Laevis oocytes". J. Physiol. 504, 169–174 (1997).

Durinx, C.; et al.; "Reference Values for Plasma Dipepidyl–Pepidase IV activity and their Association with Other Laboratory Parameters". Clin Chem Lab Med 2001, Feb.; 39 (2) :155–9, 1 page.

Gossrau, R.; "Cytochemistry of Membrane Proteases". Histochem J, 1985, Jul.; 17 (7) :737–71, 1 page.

Hahn, T.; et al.; "Enzyme Histochemical Evidence for the Presence of Potential Blood Pressure Regulating Proteases in Cultured Villous Explants from Human First Trimester Placentae". Acta Histochem 1993, Dec., 1995 (2) :185–92, 1 page.

Heymann, E.; et al.; "Has Dipeptidyl Peptidase IV an Effort on Blood Pressure and Coagulation." Klin Wochenschr, 1984, Jan., 2;62 (1) :2–10, 1 page.

Magyar, C.E.; et al.; "Proximal Tubule Na Transporter Responses are the same during Acute and Chronic Hypertension." Am J Physiol Renal Physiol, 2000, Aug.; 279 (2) :F358–69, 1 page.

Papies, B.; et al.; "Isoenzyme (Lactate Dehydrogenase, Aspartate Aminotransferase) and Dipeptidyl Peptidase IV Activity Changes in Blood Plasma Likely Indicative of Organ Involvement due to Arterial Hypertension." Cor Vasa, 1991; 33 (3) :218–26, 1 page.

Qureshi. N.U.; et al., "Endogenous Neuropeptide Y Mediates Vasoconstriction during Endotoxic and Hemorrhagic Shock". Regul Pept, 1998, Sep. 25; 75–76:215–20, 1 page.

The Merck Index, $9^{th}$ Edition, 1976, p. 773.

C.J. Bailey et al., *New Antidiabetic Drugs*, Smith–Gordon Nishimura, 1990, p. 36.

METHOD FOR THE PRODUCTION OF THIAZOLIDIN

CROSS REFERENCE TO OTHER APPLICATIONS

This application is a continuation of PCT/EP00/03213 filed Apr. 11, 2000.

FIELD OF THE INVENTION

The invention relates to a simple and industrially readily executable method of producing thiazolidine base and salts thereof.

BACKGROUND OF INVENTION

Thiazolidine can serve as an intermediate for the synthesis of aminoacyl and peptidyl thiazolidides, which have both a diagnostic and a therapeutic value as enzyme inhibitors [H.-U. DEMUTH, J. Enzyme Inhibition 3, 249 (1990)].

Since aminoacyl thiozolidides are suitable, inter alia, for the regulation of the blood sugar level in mammals, the preparation of these compounds and their parent materials using a cost-effective, commercially applicable process is of medical, pharmaceutical and economical interest [cf DE 19,616,486].

It is known that thiazolidine and thiazolidine derivatives can be obtained by refluxing aldehydes with aminoethyl sulfate or aminoethyl halides and sodium sulfide in aqueous solution under excess energy input over a period of several hours. The yields are ca 60% of theory [cf U.S. Pat. No. 4,584,407].

It is an object of the present invention, however, to provide a process for the production of thiazolidine base or the salts thereof in which no excess energy input is necessary.

SUMMARY OF THE INVENTION

Figure 2:
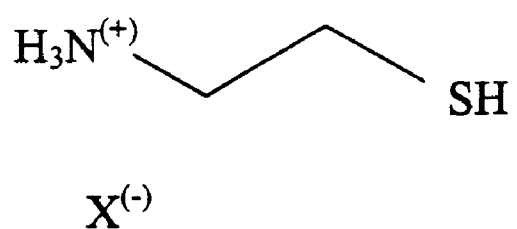

The present invention now provides a process for the production of thiazolidine base and salts thereof which is characterized in that hexamethylenetetramine of formula (I) as shown in FIG. 1 is caused to react with cyst amine or salts thereof of formula (II) as shown in FIG. 2. in which $X^{(-)}$ denotes an acid residue, $X^{(-)}$ being preferably a halide or sulfate.

It is extremely surprising to find that this process gives the free base thiazolidine and salts thereof in high yields of very pure substance without it being necessary to apply excess quantities of heat during the reaction. This constitutes a cost-effective and technological advantage of the process of the invention particularly as regards the industrial production of thiazolidine [cf EP 0,054,409].

DETAILED DESCRIPTION

In the present invention, the reaction can take place, eg, in a polar solvent such as an alcohol. Preferred solvents are methanol and/or ethanol.

Another economical and technological advantage of the process of the invention for the industrial production of thiazolidine is the fact that hexamethylenetetramine is acceptable as regards the pharmaceutical use of the secondary products of thiazotidine, since it is pharmaceutically acceptable: for many years it has been used as a urine disinfectant and for food preservation [cf Mutschler, Arzneimittelwirkungen, pp. 572 et seq., Stuttgart: Wissenschaftliche Verlagsgs. (1986)].

Preferably, ammonia is used as the initial batch and/or is added during the reaction. By this means, synthesis can be carried to the stage of the free base in a single step [cf S. Ratner, H. T. Clarke, J. Am. Chem. Soc. 59, pp 200–206 (1937)] so that additional complicated and expensive reaction stages can be omitted.

The process of the invention, which is designed for both laboratory-scale and commercial-scale applications, is carried out, for example, by adding hexamethylenetetramine to a preferably methanolic solution of a cysteamine salt all at once or in a number of portions, as solid matter or dissolved in a solvent. The mixture can be stirred for several hours at room temperature, or it may be stirred at temperatures around 30–35° C. The stated dosing procedure can take place in reverse order if desired.

The process of the invention must not necessarily be carried out under a blanket of inert gas as in other processes [cf EP 0,695,744].

The thiazolidine produced by the process of the invention can be used as starting material for the production of pharmaceutically useful active substances. The invention is illustrated with reference to the following example.

EXAMPLE

To a solution of 1.358 kg (12 mol) of cysteamine hydrochloride, used as initial batch in 1.8 L of methanol at from 30° to 35° C., there are added 291.59 g (2.08 mol) of cystamine in two portions at a reaction temperature of from 300 to 35° C. Following the addition of the first portion of the hexamethylenetetramine there is observed a distinct exothermal reaction (ca 45° C.) with violet coloration, and the reaction mixture is cooled. Coarse precipitation of ammonium chloride commences. When the exothermal reaction has subsided (after a period of 1.5 h) the second portion of hexanethylenetetramine is added. Ammonia is fed to the batch to saturation, and 700 mL of tertbutylmethyl ether are added.

The quantitative precipitation of ammonium chloride can be regarded as a process monitor. $NH_4Cl$ is filtered off in vacuo and the filter cake is washed with the reaction solution. 300 mL of aminoethylethanolamine are placed in the solution to form a sump. Thiazolidine is purified by distillation, bp: 60–70° C., 8–10 mbar. The extremely pure substance can be obtain in a yield of 88–93%.

$^1$H NMR (200 MHz, $D_2O$) δ(ppm)=2, 80–2, 83 (t, 3J=6.45 Hz, 2 h, $NCH_2CH_2$), 3, 04–3, 19 (t, 3J=6.45 Hz, 2 h, $CH_2C$ $H_2S$), 4.05 (s, 2 h, $NCH_2S$ $^{13}$C NMR (100.5 MHz, DMSO-$d_6$) δ (ppm) 30.69 (s, $NCH_2CH_2$) 47.31 (s, $CH_2CH_2S$), 47.95 (s, $NCH_2S$) MS (MALDI-TOF) 89 (M+H)

| EA: C3H7NS | theory: | C = 40.44% | found: | C = 40.27% |
|---|---|---|---|---|
| | | H = 7.91% | | H = 8.02% |
| | | N = 15.72% | | N = 15.90% |
| | | S = 35.91% | | S = 35.73% |

What is claimed:
1. A process for the production of thiazolidine base and salts thereof, wherein hexamethylenetetramine of formula (I)

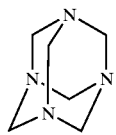

is caused to react with cysteamine or salts thereof of formula (II)

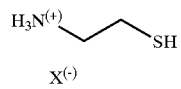

in which $X^{(-)}$ represents an acid residue.

2. A process as defined in claim 1, wherein $X^{(-)}$ is a halide or sulfate.

3. A process as defined in claim 1, wherein the reaction is carried out in a polar solvent.

4. A process as defined in claim 3, wherein the solvent is an alcohol.

5. A process as defined in claim 3, wherein the solvent is methanol or ethanol.

6. A process as defined in claim 3, wherein ammonia is added before the reaction.

7. A process as defined in claim 6, wherein ammonium salt is separated.

8. A process as defined in claim 7, wherein ammonium salt is separated.

9. A process as defined in claim 6, wherein ammonium salt is separated and the product is distilled.

10. A process as defined in claim 8, wherein ammonium salt is separated and the product is distilled.

11. A process as defined in claim 2, wherein the reaction is carried out in a polar solvent.

12. A process as defined in claim 3, wherein ammonia is added during the reaction.

\* \* \* \* \*